United States Patent
Abbondanza et al.

(10) Patent No.: US 10,821,323 B2
(45) Date of Patent: Nov. 3, 2020

(54) ALL-IN-ONE SMART CONSOLE FOR EXERCISE MACHINE

(71) Applicants: James M. Abbondanza, Lewiston, NY (US); Jackson Hsieh, City of Industry, CA (US)

(72) Inventors: James M. Abbondanza, Lewiston, NY (US); Jackson Hsieh, City of Industry, CA (US)

( * ) Notice: Subject to any disclaimer, the term of this patent is extended or adjusted under 35 U.S.C. 154(b) by 97 days.

(21) Appl. No.: 15/423,548

(22) Filed: Feb. 2, 2017

(65) Prior Publication Data

US 2017/0144025 A1 May 25, 2017

Related U.S. Application Data

(63) Continuation of application No. 15/268,619, filed on Sep. 18, 2016, now Pat. No. 9,821,191, which is a
(Continued)

(51) Int. Cl.
*A63B 24/00* (2006.01)
*A63B 71/06* (2006.01)
(Continued)

(52) U.S. Cl.
CPC ...... *A63B 24/0087* (2013.01); *A63B 24/0062* (2013.01); *A63B 24/0075* (2013.01); *A63B 71/0622* (2013.01); *G16H 20/30* (2018.01); *G16H 40/67* (2018.01); *A63B 22/0023* (2013.01); *A63B 22/0056* (2013.01);
(Continued)

(58) Field of Classification Search
CPC ............ A63B 24/0087; A63B 24/0062; A63B 71/0622; A63B 24/0075; A63B 22/0076; A63B 2220/20; A63B 22/0664; A63B 22/02; A63B 22/0056; A63B 2220/30; A63B 22/0605; A63B 2230/062; A63B 2071/0625; A63B 2071/065; A63B 2230/00; A63B 22/0023; A63B 71/0619; A63B 2225/50; A63B 2225/20; A63B 2230/06; A63B 2024/0065; G16H 20/30; G16H 40/67
See application file for complete search history.

(56) References Cited

U.S. PATENT DOCUMENTS

| | | | | |
|---|---|---|---|---|
| 5,527,239 A * | 6/1996 | Abbondanza | ..........  | A63B 22/02 482/1 |
| 6,902,513 B1 * | 6/2005 | McClure | ............ | A63B 24/0006 482/4 |

(Continued)

*Primary Examiner* — Sundhara M Ganesan
(74) *Attorney, Agent, or Firm* — Raymond Y. Chan; David and Raymond Patent Firm

(57) ABSTRACT

A smart console includes a Fitness Machine Smart Console Emulator to form a smart device which includes a control module for controlling an operation of an exercise machine, a command system operatively linked to the control module for receiving exercise related information from the exercise machine and data, and a fitness analysis module operatively linked to the control module for collecting exercise related information of the exercise machine and generating an exercise result based on the exercise related information. Therefore, the smart device simplifies the configuration of the exercise machine to remotely located device to communicate with the exercise machine.

20 Claims, 5 Drawing Sheets

Related U.S. Application Data continuation of application No. 14/515,540, filed on Oct. 16, 2014, now Pat. No. 9,474,935.

(51) Int. Cl.
*G16H 20/30* (2018.01)
*G16H 40/67* (2018.01)
*A63B 22/00* (2006.01)
*A63B 22/06* (2006.01)
*A63B 22/02* (2006.01)

(52) U.S. Cl.
CPC ........... *A63B 22/0076* (2013.01); *A63B 22/02* (2013.01); *A63B 22/0605* (2013.01); *A63B 22/0664* (2013.01); *A63B 71/0619* (2013.01); *A63B 2024/0065* (2013.01); *A63B 2071/065* (2013.01); *A63B 2071/0625* (2013.01); *A63B 2220/20* (2013.01); *A63B 2220/30* (2013.01); *A63B 2225/20* (2013.01); *A63B 2225/50* (2013.01); *A63B 2230/00* (2013.01); *A63B 2230/06* (2013.01); *A63B 2230/062* (2013.01)

(56) References Cited

U.S. PATENT DOCUMENTS

| | | | | |
|---|---|---|---|---|
| 7,628,730 B1* | 12/2009 | Watterson | ............ | A63B 21/005 482/8 |
| 7,811,201 B1* | 10/2010 | Mikan | ................ | A63B 24/0062 482/4 |
| 7,938,752 B1* | 5/2011 | Wang | ................. | A63B 24/0087 434/247 |
| 7,985,164 B2* | 7/2011 | Ashby | .................... | A63B 22/02 434/247 |
| 8,029,415 B2* | 10/2011 | Ashby | ................. | G06F 19/3481 482/49 |
| 8,317,658 B2* | 11/2012 | Dorogusker | ....... | A63B 24/0084 482/8 |
| 8,876,661 B2* | 11/2014 | Lu | ...................... | A63B 71/0619 482/1 |
| 9,028,370 B2* | 5/2015 | Watterson | ........... | G06F 19/3481 482/8 |
| 9,174,085 B2* | 11/2015 | Foley | ................. | A63B 24/0075 |
| 9,186,549 B2* | 11/2015 | Watterson | .......... | A63B 24/0062 |
| 9,364,714 B2* | 6/2016 | Koduri | .............. | A63B 24/0087 |
| 2010/0062818 A1* | 3/2010 | Haughay, Jr. | ...... | A63B 24/0062 463/7 |
| 2011/0090092 A1* | 4/2011 | Birrell | .................... | G06Q 10/06 340/870.07 |
| 2012/0053016 A1* | 3/2012 | Williamson | ....... | A63B 24/0062 482/8 |
| 2013/0012357 A1* | 1/2013 | Wang | .................... | A63B 24/00 482/4 |
| 2013/0178334 A1* | 7/2013 | Brammer | ........... | A63B 71/0622 482/4 |
| 2013/0225370 A1* | 8/2013 | Flynt | .................. | A63B 24/0087 482/4 |
| 2014/0038781 A1* | 2/2014 | Foley | ................... | A63B 21/015 482/9 |
| 2016/0059079 A1* | 3/2016 | Watterson | ................ | G09B 5/02 482/4 |

\* cited by examiner

ALL-IN-ONE SMART CONSOLE FOR EXERCISE MACHINE

CROSS REFERENCE OF RELATED APPLICATION

This is a Continuation-In-Part application that claims the benefit of priority under 35 U.S.C. § 120 to a non-provisional application, application Ser. No. 15/268,619, filed Sep. 18, 2016, which is a Continuation application that claims the benefit of priority under 35 U.S.C. § 120 to a non-provisional application, application Ser. No. 14/515,540, filed Oct. 16, 2014. The afore-mentioned patent applications are hereby incorporated by reference in their entireties.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to an exercise machine, and more particularly to an all-in-one smart console equipped in an exercise machine, which simplifies the configuration among the console of the exercise machine, the portable wireless communication device, and the server, so as to enhance the mutual efficiency of each of the exercise machine, the portable wireless communication device, and the server, and to allow the all-in-one smart console to act as an autonomous machine control system, containing all of the communication, command, control, analysis and display hardware, firmware, and software, necessary to completely manage the training or exercise with the exercise machine.

Description of Related Arts

A conventional exercise machine, such as a treadmill, usually comprises a running platform and a control link provided in front of the running platform for allowing a user to communicatively link to a portable wireless communication device of the user, such as mobile phone or tablet, in order to control the operation of the running platform. Since different users will use the same exercise machine, the users are able to use their own portable wireless communication devices to wirelessly link to the exercise machine, such that exercise-related information can be transmitted from the exercise machine to the portable wireless communication device. The user is able to download a corresponding application in the portable wireless communication device to store and analyze the exercise-related information. Therefore, the user is able to create a personal profile to control the exercise machine. However, the storage space of the portable wireless communication device is limited so that the storage space of the portable wireless communication device will be eventually full when the exercise-related information is accumulatively saved in the portable wireless communication device. Furthermore, the microprocessor of the portable wireless communication device must be powerful enough to analyze the exercise-related information. In other words, the battery life of the portable wireless communication device will be shortened in order to execute the analysis of the exercise-related information.

Therefore, the conventional advanced exercising system further incorporates with a network server to directly store, update, and analyze the exercise-related information from the exercise machine, wherein the portable wireless communication device can only access the network server to view the exercise-related information therein. After analyzing the exercise-related information, the network server of the conventional system could be arranged to automatically program and control the exercise machine corresponding to the exercise-related information. For example, when the heart rate of the user is detected above a threshold calculated corresponding to the exercise-related information, the network server will send a deactivating signal to the exercise machine to turn off the exercise machine. Therefore, the network server will automatically control the exercise machine to prevent the user being over-exercising. However, it is dangerous to adjust the machine, such as the speed and the resistance of the machine, during the exercise or to stop the exercise machine suddenly when the user is exercising. In fact, the exercise machine should be only controlled by the user because only the user understands his or her own healthy habits and efforts.

SUMMARY OF THE PRESENT INVENTION

The invention is advantageous in that it provides an all-in-one smart console for an exercise machine, which simplifies the configuration among the exercise machine, the portable wireless communication device, and the server, so as to enhance the mutual efficiency of each of the exercise machine, the portable wireless communication device, and the server.

Another advantage of the invention is to provide an all-in-one smart console equipped in the exercise machine, which acts as an autonomous machine control system, containing all of the communication, command, control, analysis and display modules, firmware, and software, necessary to completely manage the training or exercise of a user on the exercise machine. In which, the system of the all-in-one smart console can be updated via IR, BT, WIFI, ANT, or the like in a wireless manner.

Another advantage of the invention is to provide an all-in-one smart console, which is able to function independently of the portable wireless communication device.

Another advantage of the invention is to provide an all-in-one smart console, which is the only one device to compute and analyze exercise related information from the exercise machine to generate an exercise result. Therefore, no software is required to install in the portable wireless communication device or in any alternative networked device to run the computation and analysis of the exercise related information.

Another advantage of the invention is to provide an all-in-one smart console, wherein no memory is required for the portable wireless communication device to store any exercise related information from the exercise machine or updated fitness information of the user.

Another advantage of the invention is to provide an all-in-one smart console, which is able to wirelessly connect to any external fitness equipment in order to collect the exercise related information from the external fitness equipment.

Another advantage of the invention is to provide an all-in-one smart console, which is adapted to incorporate with any existing exercise machine to provide a completely control of the exercise machine. Therefore, the present invention does not require to alter the original structural design of the exercise machine, so as to minimize the manufacturing cost of the exercise machine incorporating with the all-in-one smart console.

Another advantage of the invention is to provide an all-in-one smart console, wherein no expensive or complicated structure is required to employ in the present invention in order to achieve the above mentioned objects. Therefore, the present invention successfully provides an economic and efficient solution for integrating the exercise related information to the all-in-one smart console and for analyzing the exercise related information by the all-in-one smart console.

Additional advantages and features of the invention will become apparent from the description which follows, and may be realized by means of the instrumentalities and combinations particular point out in the appended claims.

According to the present invention, the foregoing and other objects and advantages are attained by a method for integrating exercise related information of a user from an exercise machine to a portable wireless communication device, comprising the following steps.

(A) Activate an all-in-one smart console to be communicatively linked to the portable wireless communication device.

(B) Control an operation of the exercise machine by the all-in-one smart console.

(C) While the user is exercising, collect exercise related information from the exercise machine by the all-in-one smart console.

(D) Generate an exercise result based on the exercise related information by the all-in-one smart console.

In accordance with another aspect of the invention, the present invention comprises an all-in-one smart console, which is a self-contained unit, comprising a control module for controlling an operation of the exercise machine, a command system operatively linked to the control module for receiving exercise related information from the exercise machine and data from the portable wireless communication device, and a fitness analysis module operatively linked to the control module for collecting exercise related information of the exercise machine and generating an exercise result based on the exercise related information.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 1:
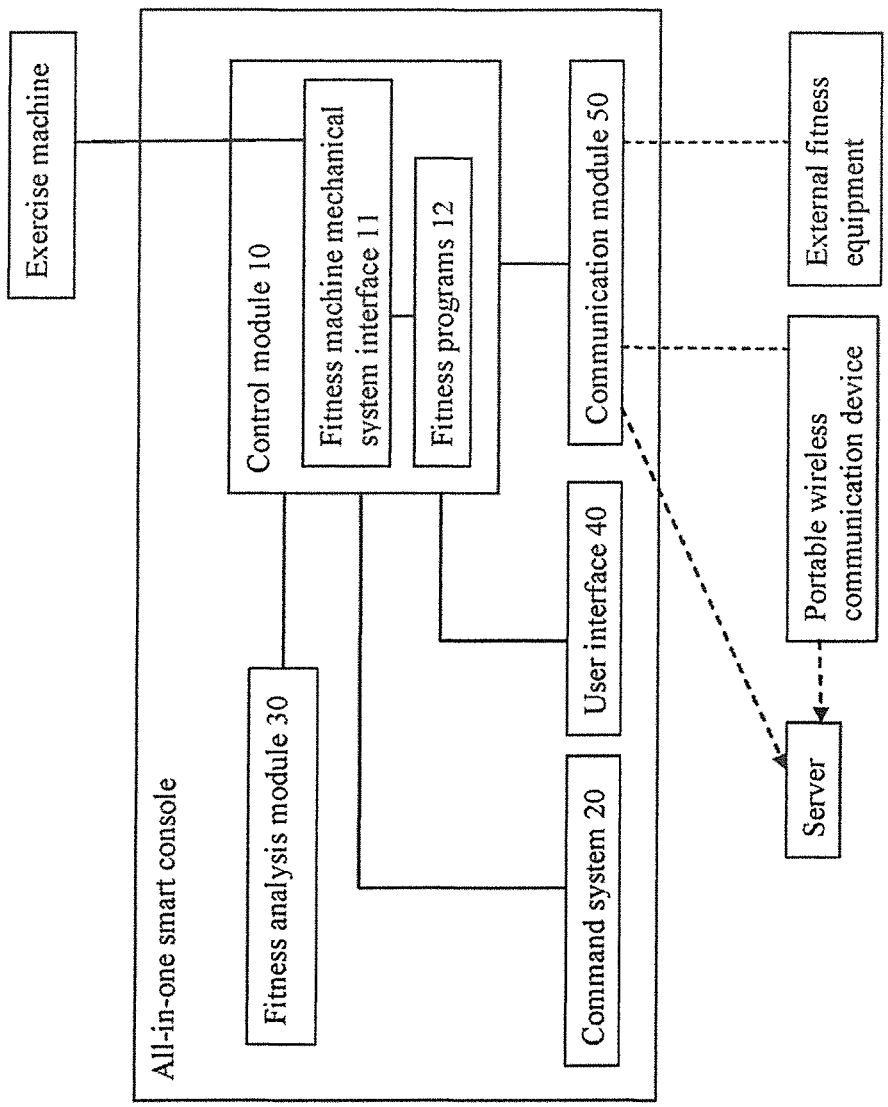
FIG. 1 is a block diagram of an all-in-one smart console according to a preferred embodiment of the present invention.

Referring to FIG. 1 of the drawings, an all-in-one smart console according to a preferred embodiment of the present invention is illustrated, wherein the all-in-one smart console is a self-contained unit to operatively link to an exercise machine and a portable wireless communication device. Accordingly, the exercise machine can be a treadmill, a stepper, an exercise cycle, an elliptical machine, or a rowing device or any other exercise or training device that requires data recording, analysis and any form of equipment motion reporting and/or control for the user to workout. The portable wireless communication device can be a mobile phone, a tablet, a PDA, or a computer.

According to the preferred embodiment, the all-in-one smart console comprises a control module 10 for controlling an operation of the exercise machine, and a command system 20 operatively linked to the control module 10 for receiving exercise related information from the exercise machine and data from the portable wireless communication device of the user. The all-in-one smart console further comprises a fitness analysis module 30 operatively linked to the control module for collecting exercise related information of the exercise machine and generating an exercise result based on the exercise related information.

The control module 10, which is a microprocessor-based master control to control the operation of the exercise machine. The control module 10 comprises a fitness machine mechanical system interface 11 to control different components of the exercise machine, such as servo, magnetic resistance, belt and lift motors. In particular, the fitness machine mechanical system interface 11 will communicates required commands to the exercise machine, and monitor and feed back the condition and/or state of the exercise machine that are receiving and executing the commands. These commands are determined by the component type of exercise machine with the commands including, but not limited to, lift up, lift down, speed up, speed down, increase or decrease mechanical tension. As a result, the portable wireless communication device cannot control the operation of the exercise machine. Instead, the portable wireless communication device must communicate with the all-in-one smart console which controls the operation of the exercise machine through the control module 10.

Figure 2:
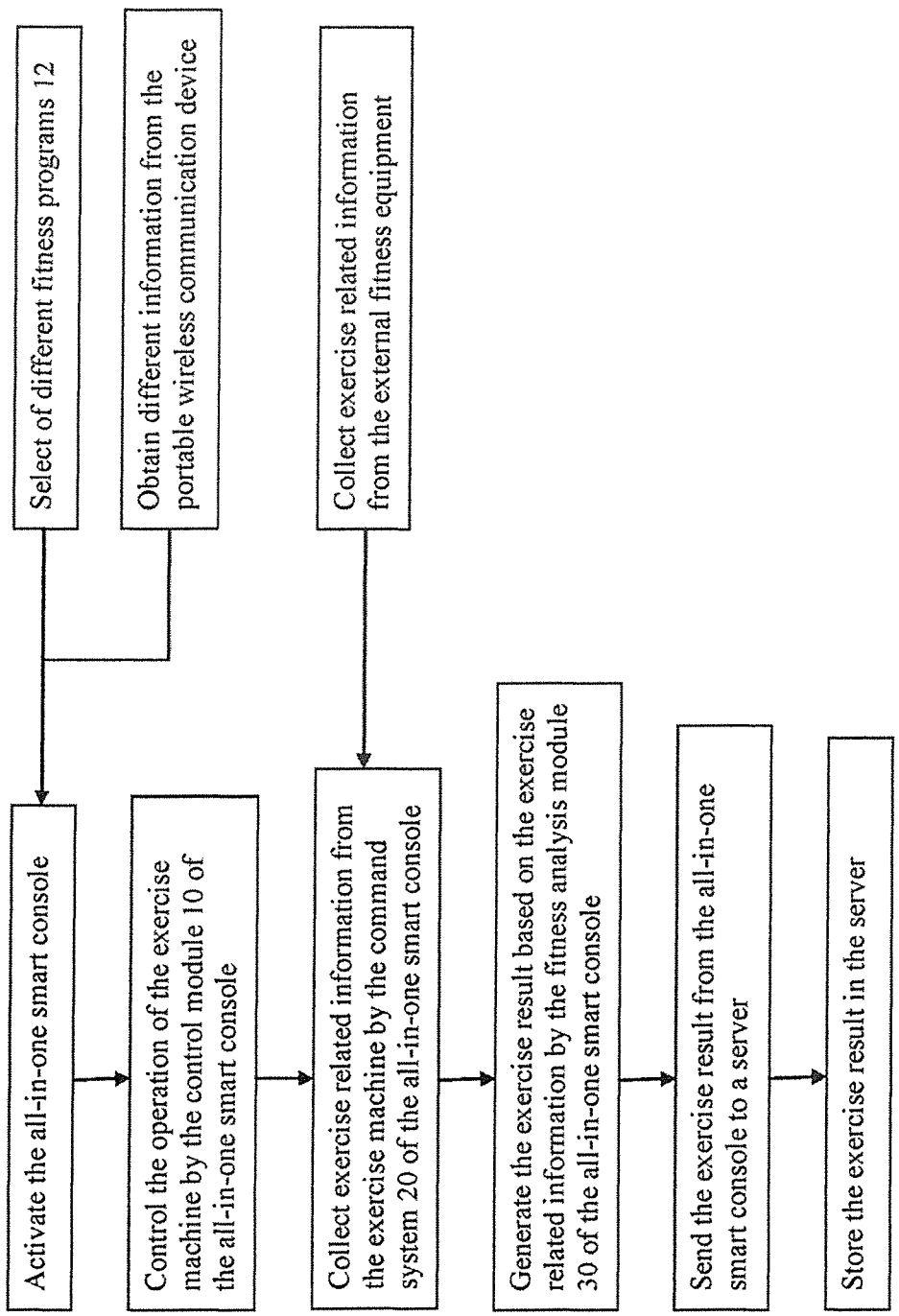
FIG. 2 is a flow diagram illustrating a method for integrating exercise related information of a user from an exercise machine to a portable wireless communication device through the all-in-one smart console according to the above preferred embodiment of the present invention.

In order to integrate the exercise related information of the user from the exercise machine to the portable wireless communication device, the present invention further provides an integration method, as shown in FIG. 2, which comprises the following steps.

(1) Activate the all-in-one smart console to be communicatively linked to the portable wireless communication device.

(2) Control the operation of the exercise machine by the control module 10 of the all-in-one smart console.

(3) While the user is exercising, collect exercise related information from the exercise machine by the command system 20 of the all-in-one smart console.

(4) Generate the exercise result based on the exercise related information by the fitness analysis module 30 of the all-in-one smart console.

(5) Send the exercise result from the all-in-one smart console to a server in such a manner that the portable wireless communication device is able to view the exercise result in the server. Or, alternatively, send the exercise result from the all-in-one smart console to a server via the portable wireless communication device which acts as a transmission device for data transmission.

(6) Store the exercise result of the user in the server as stored data for enabling the user to view only. Update the user's exercise data in the all-in-one smart console with the stored data in the server through the Internet or the portable wireless communication device which simply functions as means for transmitting data.

According to the preferred embodiment, the all-in-one smart console further comprises a user interface 40 controlled by the control module 10 for communicating with the portable wireless communication device that the portable wireless communication device serves as a remote display and input device only for the control module 10. When the control module 10 is activated in the step (1), the user interface 40 will automatically search for the portable wireless communication device. Once the portable wireless communication device is connected, preferably wirelessly connected, to the user interface 40, the user interface 40 will use the portable wireless communication device as a means for inputting and/or transmitting data to obtain user personal information, user biometric information, training options information, and/or data transmission information from the portable wireless communication device.

It is worth mentioning that the all-in-on smart console can also provide its built-in or remote input and display system, such as a monitor, touch screen, touch pad, key board, and etc., in the exercise machine for the user to input those information and interact directly with the all-in-one smart console. It is also a foreseeing alternative mode to pre-set the information in the portable wireless communication device by the user as a pre-configuration setting, such that once the connection between the user interface 40 and the portable wireless communication device is established, the information would be automatically received by the control module 10 through the user interface 40. Therefore, the portable wireless communication device will still serve as the input device of the control module 10 of the all-in-one smart console.

For example, an information program/application can be pre-installed into the portable wireless communication device to save the information. The user personal information contains screen name, first and last name of the user, address information, gender, birthday, user email address, and/or password. The user biometric information contains height, weight, displayed unit of measure, and/or activity level. The training options information contains exercise time, distance, and/or calories. The data transmission information contains information of the control module 10 and the server to be linked to the control module 10. The wireless connection between the control module 10 and the portable wireless communication device can be in form of "Bluetooth", "A.N.T.", "Infra-Red, "WiFi", or any other wireless data transfer technology. It should be appreciated that the portable wireless communication device can be connected to the control module 10 by cable.

According to the preferred embodiment, the portable wireless communication device will not receive any health parameter corresponding to the user's disease state or condition, or user's health, nutrition, fitness or exercise state or condition while the information application is running in the portable wireless communication device. In other words, a common portable wireless communication device does not contain any personal digital assistant with wireless connectivity running the information application for accepting inputs of health parameter corresponding to the user's disease state or condition, or to the user's health, nutrition, fitness or exercise state or condition.

In the step (1), according to the preferred embodiment, once the control module 10 of the all-in-one smart console is activated to link with the portable wireless communication device, the portable wireless communication device serves as a remote display and input device only, so as to restrict the exercise related information to be exchanged between the all-in-one smart console and the portable wireless communication device. For example, for the treadmill or the elliptical machine, the exercise related information of the all-in-one smart console, such as the exercise level, elapsed time, calories, speed (MPH), distance (MILE), and pulse (BPM), will be displayed on the screen of the portable wireless communication device. Accordingly, any exercise related information in the all-in-one smart console can be displayed in the portable wireless communication device. For example, heart rate received from the all-in-one smart console can be displayed on the portable wireless communication device. Therefore, the user is able to view the exercise related information during exercising. In addition, as mentioned above, the all-in-one smart console is provided with its input and viewing system, so that when the user does not carry a portable wireless communication device during exercise, the user may still access the exercise related information through the screen of the input and display system of the all-in-one smart console.

Accordingly, the user interface 40 will also transmit the display data to the portable wireless communication device to display the status of the control module 10. For example, digital video and/or audio will be transmitted to the portable wireless communication device to show the status of the control module 10. Therefore, the portable wireless communication device not only serves as the input device but also serves as a display device of the control module 10 of the all-in-one smart console. Similarly, the user may also select to access such digital video and/or audio display data through the built-in input and display system of the all-in-one smart console of the exercise machine.

The control module 10 further comprises a plurality of different fitness programs 12 to be selected via the portable wireless communication device. In response to different fitness levels of the user, the user is able to select one of the fitness programs 12 in the control module 10 by the built-in input and display system of the all-in-one smart console of the exercise machine or the portable wireless communication device functioning as the input device. Once the fitness program is selected, the operation of the exercise machine will only be controlled by the control module 10 in the step (2). For example, a plurality of activation controls, such as "pause" and "stop" controls, are provided at the all-in-one smart console, such that the user is able to actuate the activation controls to control the operation of the exercise machine. Preferably, the screen of the all-in-one smart console can be a touch screen, wherein the activation controls are provided on the screen for the user to control by means of a touch.

According to the step (3), the command system 20 will collect the exercise related information from the exercise machine during the user is exercising. It is worth mentioning that the exercise machine will only be controlled by the control module 10 while the user is exercising, such that there is no control of the exercise machine by the portable wireless communication device. In other words, the portable wireless communication device is preferred to merely function as the input device for the user to input information and make selection of programs and functions of all-in-one smart console remotely and the display device for the user to access information from the all-in-one console of the exercise machine. Furthermore, the portable wireless communication device has no need to store the exercise related information from the exercise machine. Therefore, no memory is required in the portable wireless communication device to store such exercise related information. All the exercise related information is preferred to be collected by the all-in-one smart console.

It is worth mentioning that the portable wireless communication device does not provide any exercised related information or receive data indicating a physiologic status of the user directly from the user, especially while the user is exercising.

The all-in-one smart console is able to communicate with an external fitness equipment, such as a heart rate transmitter worn by the user. In particular, the all-in-one smart console further comprises a communication module 50 operatively linked to the control module 10 for wirelessly connecting with the external fitness equipment so as to collect the exercise related information from the external fitness equipment to the command system 20. For example, the communication module 50 can wirelessly link to the heart rate transmitter, such that a user heart rate will only be collected by the all-in-one smart console via the heart rate transmitter worn by the user in order to generate the exercise result. It is worth mentioning that the user heart signal will not be transmitted to the portable wireless communication device in order to control the all-in-one smart console of the exercise machine by the portable wireless communication device. In other words, since the portable wireless communication device will only function as a remote display and/or an input device of the all-in-one smart console, the portable wireless communication device will not effect or control any changes in the exercise parameters of the user, will not send any information to the external fitness equipment, and will not store or update any exercise related information from the external fitness equipment, such that the exercise related information from the external fitness equipment will not be stored in or analyzed by the portable wireless communication device. In addition, the exercise related information from the external fitness equipment will not be stored in the memory of the external fitness equipment. The wireless connection between the communication module 50 and the fitness equipment can be in form of "Bluetooth", Radio frequency (RF), Infrared (IR), or "WiFi". It is worth mentioning that the connection between the control module 10 and the portable wireless communication device is formed via the communication module 50.

It is worth mentioning that, during the exercise, fitness information and exercise information corresponding to the exercise will only be updated directly to the fitness analysis module 30 of the all-in-one smart console. In other words, during the exercise, no fitness information will be updated to the fitness analysis module 30 and no exercise information corresponding to the exercise will be sent to the exercise machine through the portable wireless communication device for changing the exercise machine setting or predetermined routine fitness information. Therefore, the portable wireless communication device has no need to contain any exercise communication module that can send a subset of updated fitness information during the user workout.

Once the workout is completed, all the exercise related information from the exercise machine will be automatically collected. The exercise related information will then be analyzed by the fitness analysis module 30 to generate the exercise result. In other words, the calculation and analysis of the exercise related information will be performed by the fitness analysis module 30 of the all-in-one smart console but not by the portable wireless communication device. Accordingly, the exercise result may will measure the strength and weakness of the user with fitness assessments. Therefore, the exercise result may will show the before and after workout and/or compare the current exercise result with the previous exercise result(s) to measure the improvement of the physical fitness of the user. It is worth mentioning that the all-in-one smart console is prohibited to communicate with the server until the exercise result generated by the all-in-one smart console has been sent to the server, such that no exercise related information will be sent to the server during the user is exercising.

The exercise result will be sent to the server, such as a "cloud server" for the user to view. The server and the all-in-one smart console will combined to form an exercise system for integrating exercise related information of the user from the exercise machine to the portable wireless communication device. Accordingly, once the workout is completed, a notification will be generated by the control module 10 to notify the generation of the exercise result. The notification will be sent to the portable wireless communication device to inform the user that the exercise result has been created by the fitness analysis module 30. Therefore, the user is able to actuate the all-in-one smart console, such as press a send button on the all-in-one smart console, or actuate the portable wireless communication device, such as touch a send button on the portable wireless communication device, in order to transmit the exercise result to the server. Person skilled in the art would understand that it would be an alternative of the present invention that the actuation of the portable wireless communication device may also to begin and execute in sequence automatically.

It is worth mentioning that since the data transmission information contains information about the server, the exercise result will send to the designated server, such as an Internet site, corresponding to the data transmission information. Preferably, the exercise result will be transmitted via the data protocol of the portable wireless communication device to the server if available. Alternatively, the exercise result can be transmitted by a way of a "WiFi-enabled" network to which the portable wireless communication device is presently connected. It should be appreciated that the exercise result can be transmitted through any network directly established between the all-in-one smart console and the server. According to the preferred embodiment, the exercise related information from the exercise machine will not be sent to the server for analysis and computation and will be analyzed and computed in the all-in-one smart console for such exercise result. In one embodiment, the server will not receive any information corresponding to the health parameter of the user from the portable wireless communication device and the exercise result computed in the all-in-one smart console is transmitted to the server from the all-in-one smart console through the Internet. In another embodiment, the portable wireless communication device can be functioned as a transmitting device while the all-in-one smart console has no internet connection with the server, wherein the exercise result computed in the all-in-one smart console is transmitted to the server via the portable wireless communication device. For example, the all-in-one smart console transmits the exercise result to the portable wireless communication device through Bluetooth or IR, and the portable wireless communication device can transmit such exercise result computed by the all-in-one smart console to the server through its Internet connection with the server.

Once the exercise result is stored in the server, the user is able to access the server at any time and any place to view the exercise result. According to the preferred embodiment, the server will not compare the personal data and/or the exercise result with other different users. In other words, the user can only view his or her own exercise result(s). However, a user may request access of another user's exercise result and information upon approval of the other user, for example though a chating or to communication APP. It is appreciated that a smart console network can be established by the smart consoles of a plurality of exercise machines forming a community of smart consoles through the communication network, such as WiFi, Bluetooth, Internet, and the like, wherein the networked smart consoles can communicate with each other for chating or information exchanging according to agreement between the networked smart consoles.

It is worth mentioning that the all-in-one smart console of the present invention will enhance the efficiency of each of the exercise machines, the portable wireless communication device, and the server, wherein each of them will effectively get its own job done individually. In other words, the all-in-one smart console will only obtain the exercise related information of the exercise machine in a real time manner to collect the information of before and after workout, such that the portable wireless communication device will not require collecting the exercise related information from the exercise machine in a real time manner. During exercising, the exercise related information will be transitionally sent to the all-in-one smart console. Therefore, the portable wireless communication device will not require large storage space to store the exercise related information. Furthermore, the user is able to carry his or her own portable wireless communication device and link to different exercise machines in any sequent order. For example, the user may first link his or her portable wireless communication device to the all-in-one smart console of a bicycle machine and exercise for a certain period of time while his or her exercise result computed by the all-in-one smart console of the bicycle machine will be stored in the server. Then, the user may link his or her portable wireless communication device to a treadmill machine and exercise for another certain period of time and his or her exercise result computed by the all-in-one smart console of the treadmill machine will also be stored in the server. Therefore, the user may also use his or her portable wireless communication device linked to server through Internet to access his or her exercise result stored in the server.

The all-in-one smart console will receive the exercise related information from the exercise machine. Then, the all-in-one smart console will send the exercise result analyzed by the all-in-one smart console to the server after exercising. Therefore, the portable wireless communication device will not require powerful calculating power to analyze the exercise related information. It is worth mentioning that multiple users can access the all-in-one smart console of any exercise machine by disconnecting one of the portable wireless communication devices from the all-in-one smart console and connecting the all-in-one smart console with another portable wireless communication device. In other words, the all-in-one smart console is activated to connect one portable wireless communication device at one time.

Person skilled in the art would understand that the exercise result in the step (5) can also be directly sent to the portable wireless communication device.

It is appreciated that the all-in-one smart console can be a computer, a dedicated internet site, or Google Chromecast type device to be connected to the exercise machine by the user for total portability to exercise in front of any television with full graphical display and remote input, which is embodied as the portable wireless communication device. In other words, the television is considered as a wireless communication device for remote input and display.

It is appreciated that the all-in-one smart console of the present invention can be alternatively a dedicated tablet computer wired directly to the exercise machine for data transmission and power, able to communicate with wireless communication devices, provide multiple user exercise programs, communicate directly with biological signal transmitters such as heart rate monitors, analyze those signals along with other user and machine supplied information to control exercise machine motors, lift and resistance systems and provide exercise related information in audio/visual form to the user.

It is appreciated that the all-in-one smart console of the preferred embodiment can be modified as a remotely located device communicating with the fitness machine and/or user via an APP on any smart mobile devices, smart televisions and other and other processing systems, including but not limited to Amazon Echo, Google Home, Apple Siri, capable of communicating directly with the fitness machine and/or user. In other words, the smart console can be a remote device (including a mobile device, TV, etc.) that communicate with the exercise machine.

In particular, the all-in-one smart console and the portable wireless communication device can be configured to have the same function by the same APP (application). It is configurable that the portable wireless communication device and/or television (smart TV) can serve as the smart console via the application.

Figure 3:
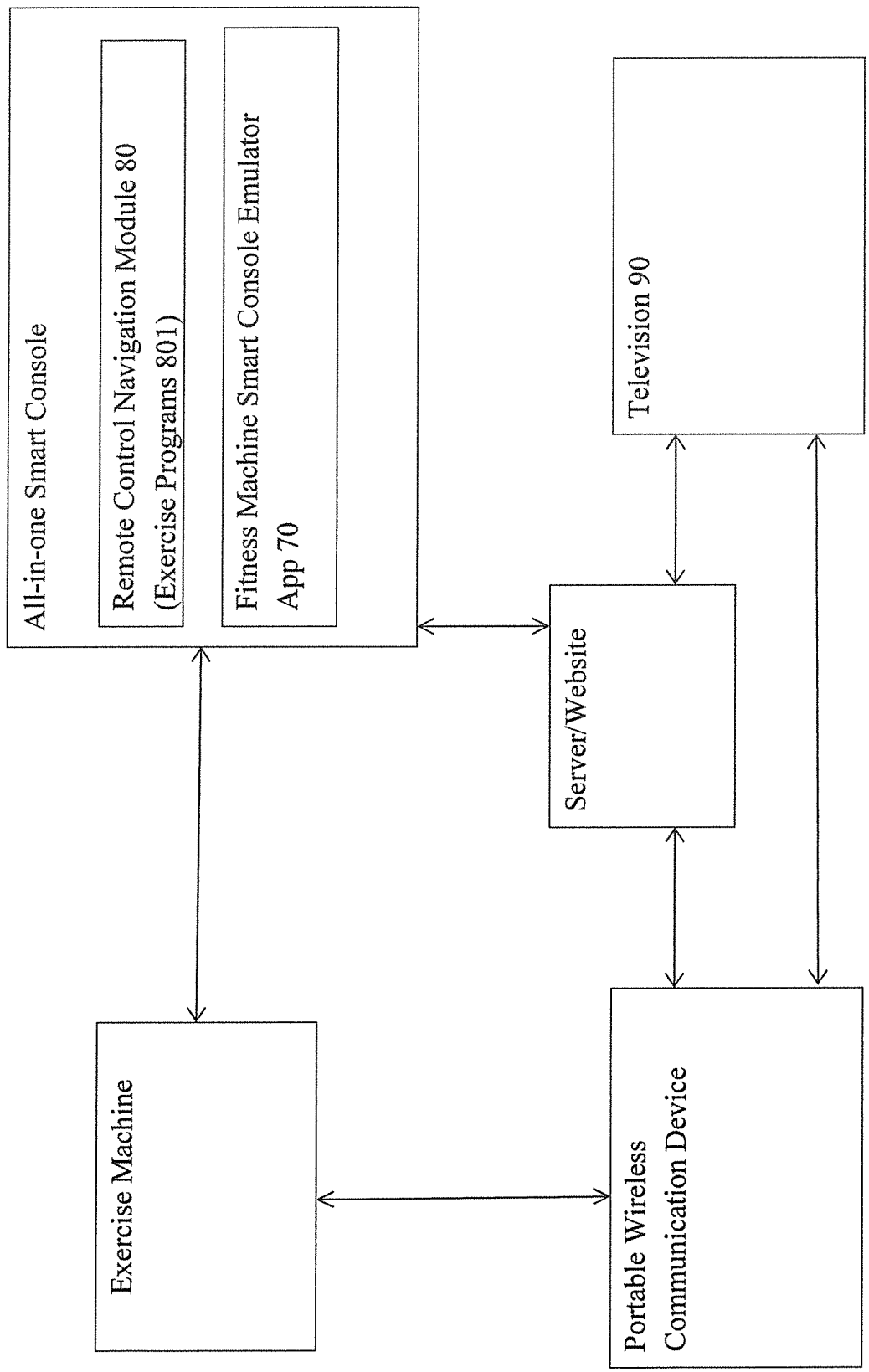
FIG. 3 is a block diagram of an all-in-one smart console according to an alternative mode of the preferred embodiment of the present invention, illustrating an all-in-one smart console communicating with the fitness machine and/or user via an APP on any smart devices.

Referring to FIG. 3 of the drawings, in one embodiment, the application is a "Fitness Machine Smart Console Emulator App 70" (CEA or FMCEA) to be installed and executed in the smart console. During the execution of the application, the smart console will form a remote control navigation module (RCM) 80 for the fitness machine or exercise machine. When the smart console is operatively linked to the portable wireless communication device wirelessly or by wire, the smart console will set up a communication link between a website (or server) and the exercise machine. It is worth mentioning that the remote control navigation module (RCM), resident on the smart console, provides all the functions for running and managing the website and the TV screen functions. In one embodiment, the remote control navigation module (RCM) can be a horizontal/vertical button assembly with up-and-down, left-and-right finger contact points and a central contact selection/accept button. Therefore, the user is able to use the smart console to control the parameters, such as speed adjustments and exercise program selections, of the exercise machine. It is worth mentioning that the smart console can be wirelessly linked to the operation module of the exercise machine via "Bluetooth", "WiFi", or other wireless connection means.

At the same time, the smart console is operatively linked to the television 90 via the portable wireless communication device, wherein the remote control and/or the operation display is projected to the television 90. Therefore, the screen of the television 90 will display the remote control and/or the operation display from the smart console. In one embodiment, the remote control and/or the operation display from the smart console is sent to the website, wherein the application will stream the display info from the website to the television screen. For example, the display info can be mirrored to display on the screen of the television. Streaming from the website to the television is accomplished by the CEA subroutine that accesses an active local WiFi or Cellular connection to communicate with the website and transfer video, sound and relevant data resulting from the user exercising on the exercise machine, such as stationary fitness bicycle, as one of many possible user/machine interactive system configurations.

Figure 4:
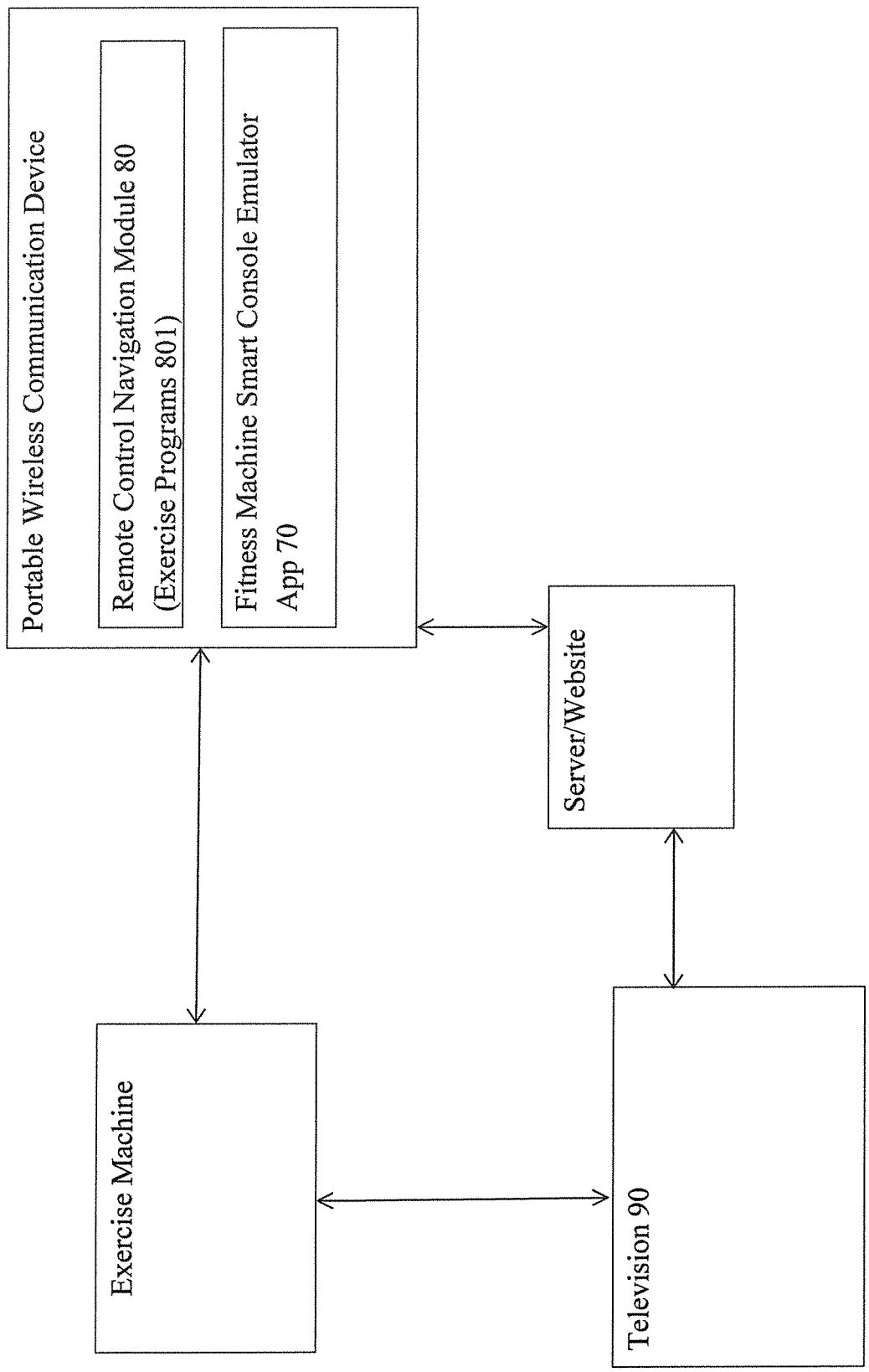
FIG. 4 is a block diagram illustrating a "Fitness Machine Smart Console Emulator App" (CEA) which can be installed and executed in the portable wireless communication device according to the above mentioned modified preferred embodiment of the present invention.

Referring to FIG. 4 of the drawings, in one embodiment, it is appreciated that the "Fitness Machine Smart Console Emulator App" (CEA) 70 can be installed and executed in the portable wireless communication device as a software package. In this example, the portable wireless communication device is a smart phone.

During the execution of the application, the smart phone will form the remote control navigation module (RCM) 80 for the fitness machine or exercise machine, wherein the smart phone will set up a communication link between the website (or server) and the exercise machine. Therefore, the remote control navigation module (RCM) 80 is resident on the smart phone, wherein the user is able to remote control the exercise machine via the smart phone. For example, the application in the smart phone will stream the website to the screen of the television that mirrors the website for the remote control and display. As the remote control positions a cursor on the smart phone, the image is mirrored on the screen of the television. In other words, the touch of the user on the touchscreen of the smart phone will be imaged and shown on the screen of the television.

In one embodiment, the magnetic pickup wired to the Bluetooth PCB provides an electrical impulse each time the magnetic pickup is activated by proximity to a stationary magnet. The BT PCB (in the control console of the exercise machine) then transmits the RPM signal to the application (CEA), within which the appropriate calculations are made (exercise duration, cadence, METS, calorie burn, distance covered, speed, etc.) for display on the screen of the television.

As shown in FIG. 4, in one embodiment, the "Fitness Machine Smart Console Emulator App" (CEA) 70 can be installed and executed in the television as the software package. In this example, the television is a smart television (STV). It is appreciated that the television can also be an Amazon Echo, a Google Home, an Apple Siri, and the like.

During the execution of the application, the smart TV will form the remote control navigation module (RCM) 80 for the fitness machine or exercise machine, wherein the smart TV will set up a communication link between the website (or server) and the exercise machine. Therefore, the remote control navigation module (RCM) 80 is resident on the smart TV, wherein the user is able to remote control the exercise machine via the smart TV by the TV remote control as an example. For example, the application in the smart TV will directly stream the website to the screen of the television that mirrors the website for the remote control and display.

Figure 5:
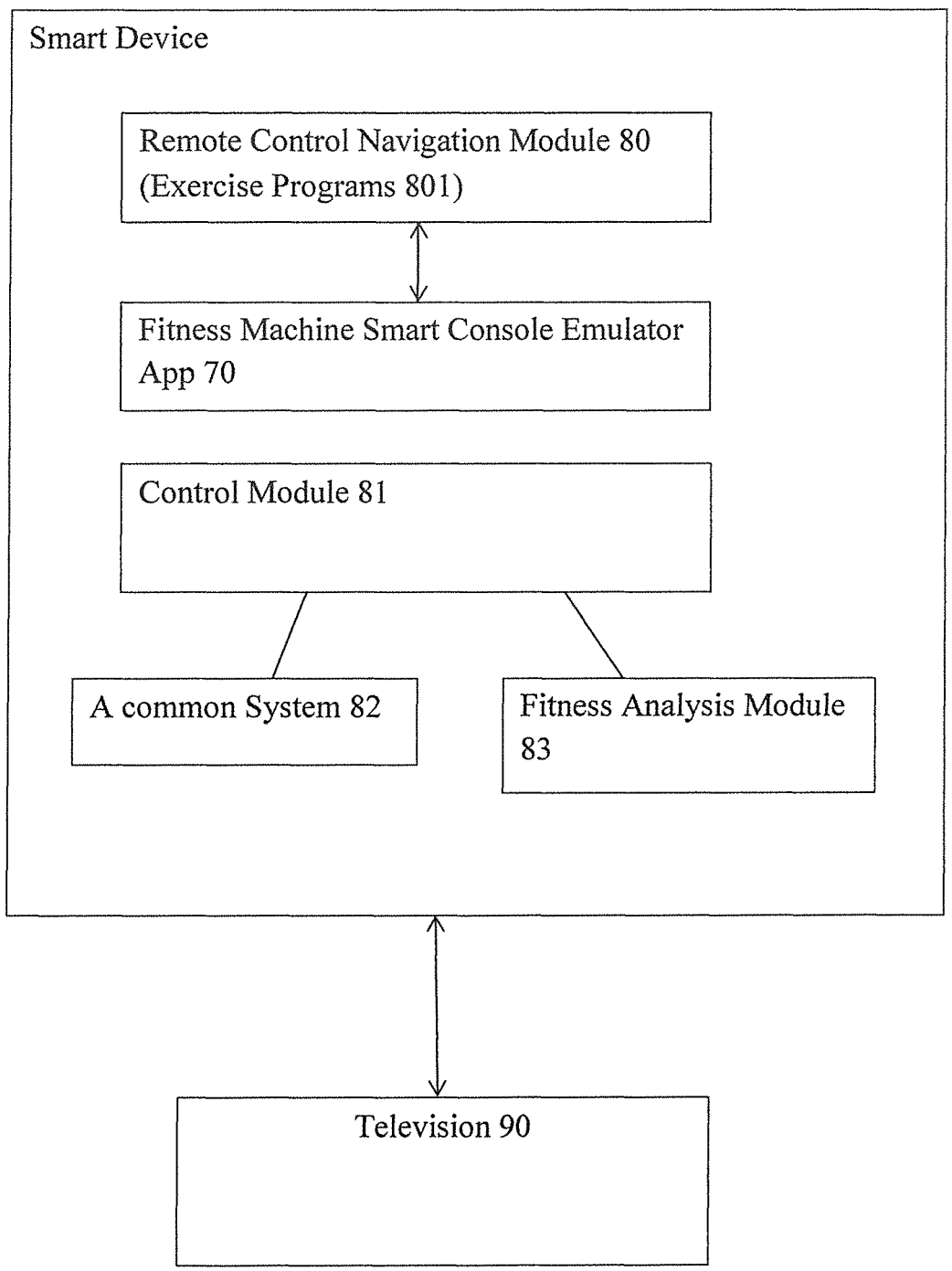
FIG. 5 is a block diagram illustrating a "Fitness Machine Smart Console Emulator App" (CEA) which can be installed into any electronic device to form the smart device for controlling and configuring the exercise machine.

Referring to FIG. 5 of the drawings, in one embodiment, it is appreciated that the "Fitness Machine Smart Console Emulator App" (CEA) 80, as a software package, can be installed into the smart console, the smart phone, or the smart TV. In other words, the "Fitness Machine Smart Console Emulator App" (CEA) 80 can be installed into any electronic device to form the smart device for controlling and configuring the exercise machine. In other words, the smart console, the smart phone, and the smart TV form the command and control device once the "Fitness Machine Smart Console Emulator App" (CEA) 80 is installed thereinto. Therefore, the smart device comprises a control module 81 for controlling the operation of the exercise machine, a command system 82 operatively linked to the control module 81 for receiving exercise related information from the exercise machine and data, and a fitness analysis module 83 operatively linked to the control module 81 for collecting exercise related information of the exercise machine and generating the exercise result based on the exercise related information.

In one embodiment, through the "Fitness Machine Smart Console Emulator App" (CEA) 70 in the smart device, the user is able to customize the personal profile in the remote control navigation module (RCM) 80 on the smart device. For example, the remote control navigation module (RCM) 80 provides different exercise programs 801, such as stationary bike, treadmill, etc, wherein the user is able to select one of the exercise programs 801 to do exercise. Then, different exercising programs 801, such as different time setting, different intensity setting, and/or different distance setting, can be pre-configured in the remote control navigation module (RCM) 80, such that the user is able to select one of the exercising programs 801 to do exercise. For example, different road conditions of the road cycling routes are preset in the remote control navigation module (RCM) 80 for the user to select. It is worth mentioning that different users are able to interact with each other via the smart device, such that different users are able to try the same exercising program 801 at the same time or at different times. For example a user A can invite a user B to do the same exercising program 801 at the same time. Likewise, the user A can invite the user B to do the same exercising program 801 after the user A finishes the exercising program 801. Therefore, the users A and B can compare their results under the same exercising program 801. It is worth mentioning that the user is able to do the customized exercising programs with different exercise machines at different locations. For example, the user is able to go to any fitness center at a vacation resort and to do the stationary bike as he or she do the stationary bike at home by simply carrying his or her smart phone with the "Fitness Machine Smart Console Emulator App" (CEA) in the smart phone and connecting the smart phone to the stationary bike wirelessly or by wire. It is worth mentioning that the user is able to customize the audio and/or video signal in the personal profile. For example, a favorite music can be preset in the personal profile, such that the user is able to play his or her favorite music during the workout.

In one embodiment, through the "Fitness Machine Smart Console Emulator App" (CEA) 70, the exercising data will be stored in the app of the smart phone if the smart phone has been configured as a Fitness Machine Smart Console Emulator App. For example, the exercising results will be saved in the personal profile. In addition, if the selected exercising program is not completed yet, the user is able to continue the exercising program next time. In other words, the exercising program will be resumed at the time when it was paused last time, so that the user is able to continuous the exercising program.

In one embodiment, the smart device can receive heart rate signals from a heart rate device worn by the user. For example, when the "Fitness Machine Smart Console Emulator App" (CEA) 70 is installed into the smart phone as the smart device, the smart device can simply display the user heart rate or provide an automatic program controlled by the user's heart rate to manage exercise machine, such as the tension level on the stationary fitness bicycle, the speed and incline of the fitness treadmill and many other configurations defined by whatever motor, servo, or other means of creating motion, resistance, and other measurable physiological functions programmed into the smart device. It is worth mentioning that the smart device can connect to different fitness or health hardware and exercise machines, such as treadmill, elliptical, stationary bike, pedometer, muscle resistance training device, IBI-HRM, RPM device, baby monitors, weight scale, blood pressure monitor, blood sugar monitor, inhaler, rehab devices, and/or multi-sensor input (up to 6), such as peripheral temperature sensors, muscle, HRM, GSP, etc.

The following example illustrates the operation of the "Fitness Machine Smart Console Emulator App" (CEA) 70 in the smart phone to form the smart device, wherein the smart device is set to operatively connect to the stationary bike. Then, through the "Fitness Machine Smart Console Emulator App" (CEA) 70, the smart phone can connect to the smart TV 90 to allow system integration. The "Fitness Machine Smart Console Emulator App" (CEA) 70 will automatically design and create the necessary webpages for the smart TV 90 to mirror. Accordingly, the signal channel is formed between the stationary bike and the smart phone, wherein the control, such as RPM, automatic control for preselected terrain and heart rate control, will be transferred to the smart phone. Therefore, the user is able to control the stationary bike by the smart phone and to view the exercising status on the smart TV 90.

Referring to FIG. 6 of the drawings, it is worth mentioning that the existing smart TVs 90 have equipped with large-screen and networking capability, wherein Internet and plug in broadcast reception devices, such as "Apple TV" or Chomecast", wherein the smart phone can project the image to the smart TV 90. In other words, the CEA 70 may not able to install into some smart TVs 90 because the television manufacturers have their own standards for TV Apps, system drivers, and application software must be customized for their own smart TVs. In this case, the "Fitness Machine Smart Console Emulator App" (CEA) 70 can be installed into the smart phone to project the info of the exercise machine to the smart TV 90. For the smart TV 90 that the user is able to download and install any App in the smart TV, the "Fitness Machine Smart Console Emulator App" (CEA) 70 can be installed into the smart TV to form the smart device.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for integrating exercise related information of a user from a mechanical exercise machine, comprising the steps of:
   (a) wirelessly and communicatively connecting a smart console to at least a control console of said exercise machine that said control console is configured to wirelessly control an operation of said mechanical exercise machine, controlling said operation of said mechanical exercise machine by said smart console; and collecting at least an exercise related information from said mechanical exercise machine by said smart console, wherein said smart console is a smart device installed with a Fitness Machine Smart Console Emulator Application which is programmed to wirelessly connect to said mechanical exercise machine, to wirelessly operate said mechanical exercise machine, and to wirelessly collect said exercise related information from said mechanical exercise machine;
   (b) generating an exercise result based on said exercise related information by said smart console by computing, calculating and analyzing said exercise related information; and
   (c) wirelessly connecting said smart console to a television and displaying said exercise related information on a screen of said television by streaming.

2. The method, as recited in claim 1, wherein said smart device is formed by downloading and installing the Fitness Machine Smart Console Emulator Application into a smart phone.

3. The method as recited in claim 2 wherein, in the step (c), said exercise related information is wirelessly sent from said smart phone to a webpage and said television is linked to said webpage to stream and display said exercise related information.

4. The method, as recited in claim 1, wherein said smart device is formed by installing the Fitness Machine Smart Console Emulator Application into said control console of said mechanical exercise machine.

5. The method as recited in claim 4 wherein, in the step (c), said exercise related information is wirelessly sent from said control console to a webpage via a wireless communication device and said television is linked to said webpage to stream and display said exercise related information.

6. The method, as recited in claim 1, wherein said smart device is formed by installing the Fitness Machine Smart Console Emulator Application into said television, wherein, after installing the Fitness Machine Smart Console Emulator Application, said smart device is adapted to communicate with other smart devices to form a network.

7. The method as recited in claim 6 wherein, in the step (c), said exercise related information is directly and wirelessly sent to said television to stream and display said exercise related information through said television having said screen.

8. The method, as recited in claim 1, wherein the step (a) further comprises a step of connecting said smart device to a fitness/health hardware for collecting measurable physiological data from the user.

9. The method, as recited in claim 1, before the step (a), further comprising a step of customizing a personal profile of the user in said smart device, wherein different mechanical exercise machines and different exercising programs are pre-set in said personal profile.

10. The method, as recited in claim 1, further comprising a step of saving said exercise related information in the Fitness Machine Smart Console Emulator Application in said smart device.

11. The method, as recited in claim 1, wherein said operation of said mechanical exercise machine is only controlled by said smart device while the user is exercising.

12. The method, as recited in claim 1, wherein said smart device is activated to serve as a remote display and input device for said mechanical exercise machine.

13. An integrated system for integrating exercise related information of a user from a mechanical exercise machine, comprising:
a Fitness Machine Smart Console Emulator for being installed into an electronic device, wherein said Fitness Machine Smart Console Emulator is configured to implement:
wirelessly and communicatively connecting to a control console of said mechanical exercise machine;
wirelessly collecting exercise related information from said mechanical exercise machine;
wirelessly controlling an operation of said mechanical exercise machine;
generating an exercise result based on said exercise related information by computing, calculating and analyzing said exercise related information; and
wirelessly connecting to a television and displaying said exercise related information on said television.

14. The integrated system, as recited in claim 13, wherein said Fitness Machine Smart Console Emulator is installed in said control console to form a smart console, wherein said smart console comprises a control module for wirelessly controlling said operation of said mechanical exercise machine, a command system operatively linked to said control module for receiving exercise related information from said mechanical exercise machine and data, and a fitness analysis module operatively linked to said control module for collecting said exercise related information of said mechanical exercise machine and generating said exercise result based on said exercise related information.

15. The integrated system, as recited in claim 14, wherein said Fitness Machine Smart Console Emulator provides a plurality of different fitness programs to be selected.

16. The integrated system, as recited in claim 14, wherein said exercise related information is wirelessly sent from said Fitness Machine Smart Console Emulator to a webpage via a wireless communication device and a television is linked to said webpage to stream and display said exercise related information on said television.

17. The integrated system, as recited in claim 14, wherein said Fitness Machine Smart Console Emulator further collects measurable physiological data from a fitness/health hardware worn by the user.

18. The integrated system, as recited in claim 14, wherein said Fitness Machine Smart Console Emulator forms a remote control navigation module in said electronic device so as to form a remote control of the mechanical exercise machine.

19. The integrated system, as recited in claim 14, wherein said Fitness Machine Smart Console Emulator stores said exercise related information from the mechanical exercise machine.

20. The integrated system, as recited in claim 14, wherein said Fitness Machine Smart Console Emulator is downloaded and installed into said electronic device to form an input device of the mechanical exercise machine.

* * * * *